US00PP37207P2

(12) United States Plant Patent
Nakata et al.

(10) Patent No.: US PP37,207 P2
(45) Date of Patent: Jan. 13, 2026

(54) MANDARIN PLANT NAMED 'Mikanken15'

(50) Latin Name: ***Citrus* spp.**
Varietal Denomination: Mikanken15

(71) Applicant: EHIME PREFECTURE, Ehime (JP)

(72) Inventors: Haruhito Nakata, Ehime (JP); Yukinori Shigematsu, Ehime (JP); Yoji Hyodo, Ehime (JP); Hiroaki Mido, Ehime (JP); Takehiro Kikuchi, Ehime (JP); Yasuyuki Masamoto, Ehime (JP); Takae Sakimoto, Ehime (JP); Hiromichi Yakushiji, Ehime (JP); Takehiro Okusada, Ehime (JP); Taizo Ninomiya, Ehime (JP); Mitsutoshi Okamoto, Ehime (JP); Saki Yamamoto, Ehime (JP); Saki Miyoshi, Ehime (JP); Toya Hioki, Ehime (JP); Kei Kinoshita, Ehime (JP); Daijiro Sugawara, Ehime (JP)

(73) Assignee: EHIME PREFECTURE, Matsuyama (JP)

( * ) Notice: Subject to any disclaimer, the term of this patent is extended or adjusted under 35 U.S.C. 154(b) by 0 days.

(21) Appl. No.: 18/944,175

(22) Filed: Nov. 12, 2024

(51) Int. Cl.
*A01H 5/08* (2018.01)

(52) U.S. Cl.
USPC ..... Plt./202

(58) Field of Classification Search
USPC ..... Plt./202
CPC ..... A01H 6/785; A01H 5/08
See application file for complete search history.

*Primary Examiner* — Keith O. Robinson
(74) *Attorney, Agent, or Firm* — Seckel IP, PLLC

(57) ABSTRACT

A new variety of *Citrus* plant named 'Mikanken15' that has dark orange fruit color, without seeds, high juiciness, orange-like flavor, ease of peeling the fruit by hand, good appearance, and good tasting qualities.

3 Drawing Sheets

Common name: Mandarin.
Botanical classification: *Citrus* spp.
Variety denomination: 'Mikanken15'.

BACKGROUND OF THE NEW VARIETY

The present invention relates to a new and distinct variety of Mandarin, *Citrus* spp., which has been given the variety denomination 'Mikanken15'.

ORIGIN OF THE VARIETY

The parent varieties are 'HAREHIME' (female parent) (not patented in the U.S., plant variety protection granted in Japan, PVP No. 1,209) and 'Ehime17' (male parent) (not patented in the U.S. nor in other countries), respectively.

The variety was developed and propagated in Uwajima, Ehime, Japan.

The variety was reproduced asexually by vegetative reproduction by top grafting one-year-old scions on rootstocks. The rootstock used was 'MIYAGAWAWASE' (not patented in the U.S. nor in other countries) as an interstock grafted onto *Poncirus trifoliata* (trifoliate orange).

In 2005, crossing the parent varieties.

In 2006, collected seeds were grown.

In 2008, they were grafted on top of rootstock.

In 2010, the first fruit was harvested.

In 2012, lines were primary selected and secondary selected, and the variety was named 'Mikanken15'.

In 2024, Breeding is completed with determination of distinct, uniform, and stable (DUS) status confirmed.

Cultivation of the variety does not require special conditions or treatments.

The variety is currently mainly intended for fruit production.

SUMMARY OF THE VARIETY

The new mandarin plant 'Mikanken15' has leaf blades with very small ratio length/width, short petiole length, very short length of petal, which distinguish 'Mikanken15' from its female parent 'HAREHIME'.

Also, the new mandarin plant 'Mikanken15' having absent or sparse density of spines, and short petiole length and very short length of petal, distinguish it notably from the comparative variety 'SEINANNOHIKARI' (not patented in the U.S., plant variety protection granted in Japan, PVP No. 17,969).

A comparison with the male parent 'Ehime17' is not available because 'Ehime17' was an old breeding line, whose states of characteristics are unknown and for which there are no long living plant materials.

A comparison with both 'HAREHIME' and 'SEINANNOHIKARI' is as follows (evaluation based on averages):

TABLE 1

| Characteristics | Reference variety 'HAREHIME' | Reference variety 'SEINANNOHIKARI' | Present variety 'Mikanken 15' |
|---|---|---|---|
| Tree: Density of spine | Absent or sparse | Dense | Absent or sparse |
| Leaf blade: ratio length/width | Medium (2.3) | Very small (1.9) | Very small (2.0) |
| Petiole: length | Long (2.0 cm) | Medium (1.5 cm) | Short (1.3 cm) |

TABLE 1-continued

| Characteristics | Reference variety 'HAREHIME' | Reference variety 'SEINANNOHIKARI' | Present variety 'Mikanken 15' |
|---|---|---|---|
| Flower: length of petal | Short (12.5 mm) | Short (13.6 mm) | Very short (7.2 mm) |

BRIEF DESCRIPTION OF THE DRAWINGS

In the accompanying drawings, which are as nearly true as is reasonable possible to make in a color illustration of this type.

Figure 1:
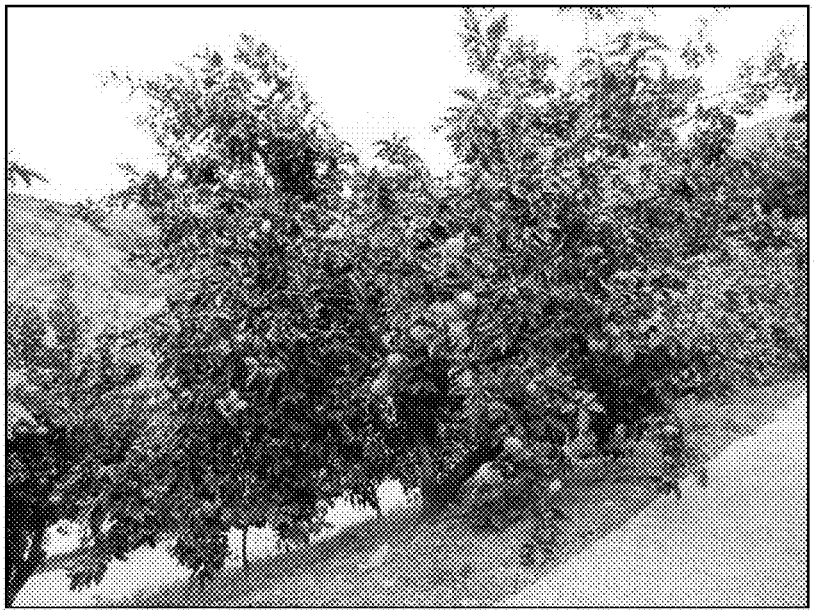
FIG. 1 is a color photograph showing a general view of the mandarin plant 'Mikanken15' bearing fruits.
Figure 2:
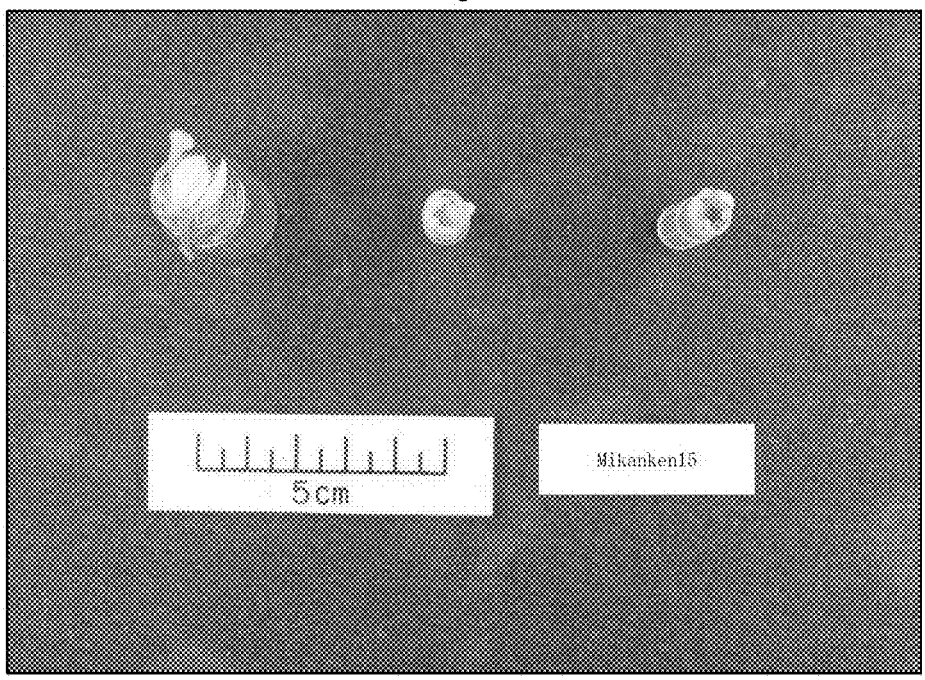
FIG. 2 is a color photograph showing flowers of 'Mikanken15'
Figure 3:
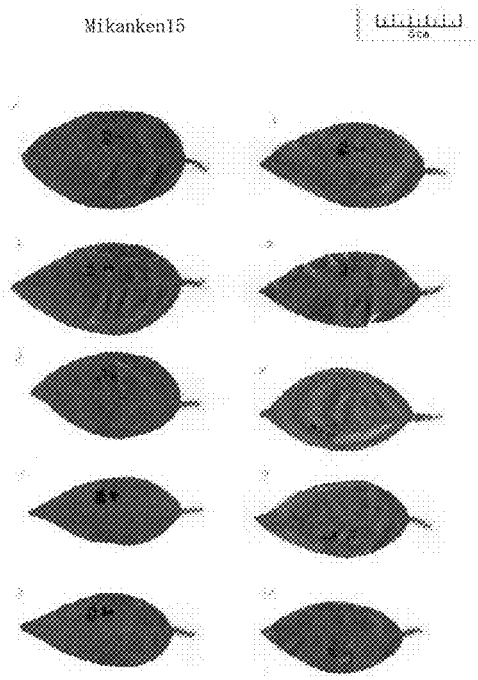
FIG. 3 is a color photograph showing leaves of 'Mikanken15'.
Figure 4:
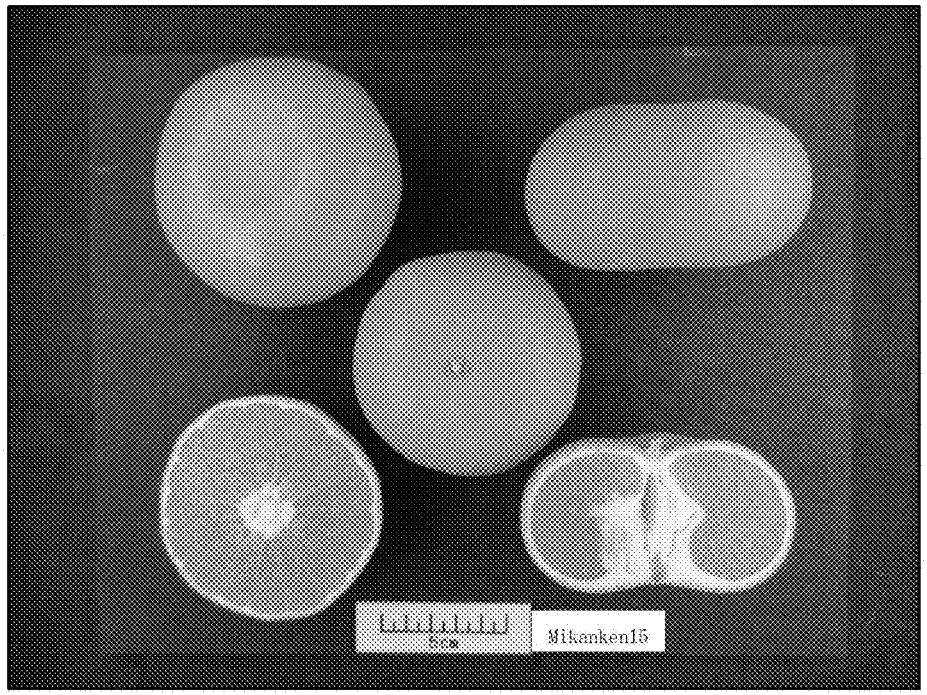
FIG. 4 is a color photograph showing fruits of 'Mikanken15'.
Figure 5:
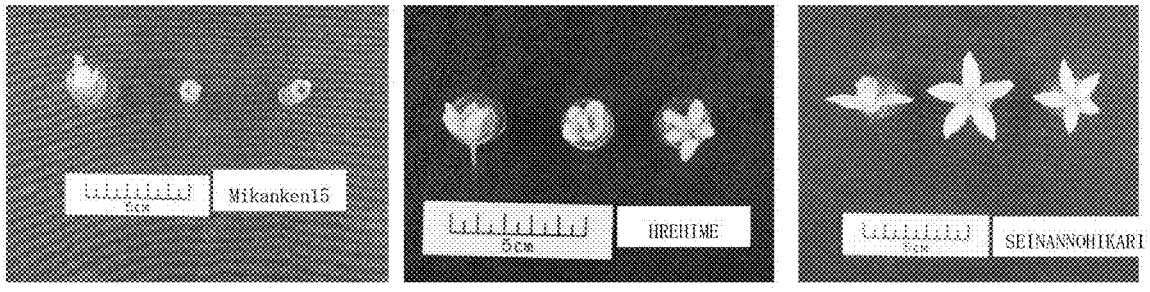
FIG. 5 is a color photograph showing the flowers of 'Mikanken15' and the comparative varieties 'HAREHIME' and 'SEINANNOHIKARI', illustrating the difference in the lower length of petals.

Due to chemical and/or digital development, processing and printing, the plants or portions of plants depicted in the photographs may or may not be precisely accurate, when compared to the actual botanical specimens.

DETAILED DESCRIPTION OF THE INVENTION

The botanical description and the photographs are of the 'Mikanken15' plants evaluated in 2023 and 2024 (including for the comparison with the reference plants 'HAREHIME' and 'SEINANNOHIKARI'). The values provided are averages.

The plants shown on the photographs were grown at Uwajima, Ehime, Japan. The plant is a 10-year old plant grown after top grafting. The tree was photographed on Dec. 3, 2023, the flowers were photographed on Apr. 25, 2024, the mature leaves were photographed on Dec. 17, 2023, and the fruit were photographed on Dec. 3, 2023. The botanical description below is that of a 10-year old plant.

Colors are given according to the Colors are given according to the J.H.S. (Japan Horticultural Society) Color Chart. (2nd edition 1997 reprint).

BOTANICAL DESCRIPTION

TABLE 2

| Characteristics | States | Values |
|---|---|---|
| Ploidy | Diploid | |
| Tree: height | | 3.6 m |
| Tree: spread | | 3.5 m |
| Tree: trunk diameter (10 cm above the graft location) | | 23 cm |
| Trunk texture | Rough | |
| Crotch angle | | 62° |

TABLE 2-continued

| Characteristics | States | Values |
|---|---|---|
| Tree: growth habit | Spreading | |
| Tree: density of spines | Absent or sparse | 5.3 |
| Tree: length of spines | | 0.3 cm |
| Branch: length | | 7.5 mm |
| Branch: diameter | | 2.9 mm |
| Branch: texture | Smooth | |
| Leaf blade: length (apical leaflet in case of compound leaf) | Medium | 9.5 cm |
| Leaf blade: width (as for No. 5) | Medium | 4.8 cm |
| Leaf blade: ratio length/width (as for No. 5) | Very small | 2.0 |
| Leaf blade: shape in cross section (as for No. 5) | Intermediate | |
| Leaf blade: twisting | Absent or weak | |
| Leaf blade: blistering | Absent or weak | |
| Leaf blade: green color | Medium | |
| Leaf blade: undulation of margin | Absent or weak | |
| Leaf blade: incisions of margin | Absent | |
| Leaf blade: shape of apex | Acute | |
| Leaf blade: emargination at tip | Absent | |
| Petiole: length | Short | 1.3 cm |
| Petiole: presence of wings | Present | |
| Varieties with petiole wings present only: Petiole: width of wings | Narrow | 2.9 mm |
| Flower: diameter of calyx | | 0.6 cm |
| Flower: length of petal | Very short | 7.2 mm |
| Flower: width of petal | Medium | 5.3 mm |
| Flower: ratio length/width of petal | | 1.4 |
| Flower: length of stamens | | 4.7 mm |
| Anther: color | Light yellow | JHS 2202 |
| Style: length | | 4.5 mm |
| Infructescence: clustering of fruits | Present | |
| Fruit: length | | 4.6 cm |
| Fruit: diameter | | 7.9 cm |
| Fruit: ratio length/diameter | Medium | 1.72 |
| Fruit: position of broadest part | At middle | |
| Fruit: shape in transverse section | Circular | |
| Fruit: general shape of proximal part (excluding neck, collar and depression at stalk end) | Flattened | |
| Fruit: presence of neck | Absent | |
| Only varieties without fruit neck: Fruit: presence of depression at stalk end | Present | |
| Only varieties without fruit neck: Fruit: depth of depression at stalk end | | 4.3 mm |
| Fruit: presence of constriction at stalk end | Absent | |
| Fruit: number of radial grooves at stalk end | Intermediate | |
| Fruit: length of radial grooves at stalk end | | 9.6 mm |
| Fruit: presence of collar | Absent | |
| Fruit: abscission layer between floral disc and fruit | Absent or weakly developed | |
| Fruit: general shape of distal part (excluding nipple, bulging of navel and depression at distal end) | Flattened | |
| Fruit: presence of depression at distal end | Present | |
| Fruit: depth of depression at distal end | | 2.1 mm |
| Fruit: diameter of depression at distal end | | 32.4 mm |
| Fruit: presence of areola | Incomplete | |
| Fruit: Type of areola | Smooth | |
| Fruit: Diameter of areola | | 1.7 cm |
| Fruit: diameter of stylar scar | | 2.1 mm |
| Fruit: persistence of style | None | |
| Fruit: presence of navel opening | Absent | |
| Fruit: presence of radial grooves at distal end | Absent | |

TABLE 2-continued

| Characteristics | States | Values |
|---|---|---|
| Fruit surface: predominant color(s) | Medium orange | JHS 1605 |
| Fruit surface: glossiness | Medium | |
| Fruit surface: roughness | Smooth | |
| Fruit surface: size of oil glands | All more or less the same size | |
| Fruit surface: size of larger oil glands | Small | |
| Fruit surface: conspicuousness of larger oil glands | Strong | |
| Fruit surface: presence of pitting and pebbling on oil glands | Pitting and pebbling absent | |
| Fruit rind: thickness | Thin | 2.2 mm |
| Fruit rind: adherence to flesh | Weak | |
| Fruit rind: strength | Medium | |
| Fruit rind: oiliness | Dry | |
| Fruit rind: conspicuousness of oil glands on inner surface | Absent or weakly conspicuous | |
| Fruit: color of albedo | White | JHS 2502 |
| Fruit: density of albedo | Loose | |
| Fruit: amount of albedo adhering to flesh (strands excluded) | Small | |
| Fruit: presence of albedo strands | Present | |
| Fruit: Amount of albedo strand | Medium | |
| Fruit: main color of flesh | Dark orange | JHS 1607 |
| Fruit: filling of core | Sparse | |
| Fruit: diameter of core | Large | 20.1 mm |
| Fruit: presence of rudimentary segments | Absent or very weak | |
| Fruit: number of well-developed segments | | 15 |

TABLE 2-continued

| Characteristics | States | Values |
|---|---|---|
| Fruit: coherence of adjacent segment walls | Medium- | |
| Fruit: strength of segment walls | Weak | |
| Fruit: length of juice vesicle | | 4.0 mm |
| Fruit: thickness of juice vesicles | | 2.3 mm |
| Fruit; conspicuousness of juice vesicle walls | Medium | |
| Fruit: coherence of juice vesicles | Medium | |
| Fruit: presence of navel (viewed internally) | Absent or very rare | |
| Fruit: juiciness | High | |
| Fruit juice: total soluble solids | High | 14.9 |
| Fruit juice: acidity | Low | 0.91 |
| Fruit: strength of fiber | Weak | |
| Fruit: number of seeds (open pollination) | Absent or very few | 0 |
| Seed: polyembryony | Absent | |
| Time of maturity of fruit for consumption | Very early to early | January |
| Fruit: parthenocarpy | Present | |
| Fruit productivity (pounds or bushels per acre) | | Not examined |

Other features of the plant are as follows:

Disease and pest resistance: Not observed to date.

Tree hardiness: USDA Hardiness Zone 9b.

The invention claimed is:

1. A new and distinct variety of *Citrus* plant named 'Mikanken15', substantially as described and illustrated herein.

* * * * *